United States Patent [19]

Ulrich et al.

[11] Patent Number: 5,688,653
[45] Date of Patent: Nov. 18, 1997

[54] 3-ALKYLAMINO-2-HYDROXY-4-HYDROXYMETHYL-2-CYCLOPENTEN-1-ONE ADVANCED GLYCOSYLATION ENDPRODUCTS AND METHODS OF USE THEREFOR

[75] Inventors: Peter C. Ulrich, Old Tappan, N.J.; Xini Zhang, Wilmington, Del.

[73] Assignee: The Picower Institute for Medical Research, Manhasset, N.Y.

[21] Appl. No.: 673,217

[22] Filed: Jun. 27, 1996

[51] Int. Cl.$^6$ .......................... G01N 33/53; C07C 205/00; C07K 16/00

[52] U.S. Cl. .................. 435/7.1; 568/305; 530/387.1; 530/389.1

[58] Field of Search .................. 568/305; 530/387.1, 530/389.1; 435/7.1

Primary Examiner—Lila Feisee
Assistant Examiner—Susan Ungar
Attorney, Agent, or Firm—Klauber & Jackson

[57] ABSTRACT

The present invention relates to advanced glycosylation endproducts (AGEs), and particularly to novel cyclopentenone aminoreductones, 3-alkylamino-2-hydroxy-4-hydroxymethyl-2-cyclopenten-1-ones. Such AGEs can be used in various diagnostic and therapeutic methods.

3 Claims, No Drawings

3-ALKYLAMINO-2-HYDROXY-4-HYDROXYMETHYL-2-CYCLOPENTEN-1-ONE ADVANCED GLYCOSYLATION ENDPRODUCTS AND METHODS OF USE THEREFOR

BACKGROUND OF THE INVENTION

The present invention relates generally to the aging of proteins and other amino-containing-biomolecules resulting from reaction of glucose, and particularly to the non-enzymatic glcation or glycosylation of proteins and other susceptible amine-presenting molecules and subsequent reactions leading to advanced glycosylation end products, and to methods for their use.

The reaction between glucose and proteins has been known for many years. Its earliest manifestation was in the appearance of brown pigments during the cooking of food, which was identified by Maillard in 1912, who observed that glucose or other reducing sugars react with amino-containing compounds, including amino acids and peptides, to form adducts that undergo a series of dehydrations and rearrangements to form stable brown pigments.

In the years that followed the initial discovery by Maillard, food chemists studied this reaction in detail and determined that stored and heat-treated foods undergo non-enzymatic browning as a result of the reaction between glucose and the polypeptide chain, and that the proteins are resultingly crosslinked and correspondingly exhibit decreased bioavailability. At this point, it was determined that the pigments responsible for the development of the brown color that evolves as a result of protein glycosylation possessed characteristic spectra and fluorescent properties.

As a result of the recent interest in this area, the first few stages of the Maillard reaction, and a relatively limited number of associated initial adducts and products, have become well-known. As subsequent reactions (including various dehydrations, oxidations, eliminations, condensations, cleavages, and other chemical changes) occur, however, a bewildering array of "early" and "late" glycation adducts and reactants is generated, and these are less well understood in molecular detail. As a group, the more advanced glycation adducts can be described as a class of yellow-brown, fluorescent pigments with intra- and intermolecular crosslinking activity, wherein specific glycation entities are thought to occur at low abundance within the widely divergent pool of advanced glycation end products (or AGEs). Despite significant work over the last twenty years or so, the molecular structures of only a few of these later glycation adducts and products have been determined, and the contribution of identified, in vivo-formed advanced glycation structures to specific biological processes remains poorly understood.

Advanced glycosylation endproducts (AGEs) have been linked to the development of many of the long-term complications of diabetes, renal insufficiency, and normal aging. Although the structures of the most abundant AGEs which occur in vivo are unknown, Monnier et al. recently isolated the fluorescent crosslink pentosidine from human dura collagen. Pentosidine appears to form as the condensation product of lysine, arginine, and a reducing sugar precursor. In vitro, pentosidine may be readily produced upon incubation of the N-alpha-protected derivatives of arginine, lysine, and sugars such as ribose, glucose, fructose, ascorbate, or dehydroascorbate.

Measurements of pentosidine content in a variety of biological specimens have revealed that this bi-functional condensation product accounts for only a small percentage (<1%) of potential glucose-derived crosslinks. Furthermore, when bovine serum albumin (BSA), which contains 59 lysine and 23 arginine residues, is incubated with D-glucose in phosphate buffer, pentosidine forms in a yield of only 1 mmol/mol protein. It also has been noted that while many proteins such as ovalbumin and BSA can undergo a high degree of modification or "impairment" of lysine and arginine residues during advanced glycosylation, protein oligomerization rarely ensues.

A large body of evidence has been assembled to show that Maillard products as a whole underlie a wide variety of both normal and pathogenic activities and responses that occur as advanced glycation end products (or AGEs) accumulate in vivo. Such activity may be direct, as a consequence of the chemical reactivity of glycation products and adducts, or indirect, mediated by the cellular recognition of glycation adducts and products via AGE-specific binding proteins or receptors. An appreciation for the pathogenic potential of AGEs has suggested that interference with, or inhibition of, advanced glycation chemistry could be of enormous therapeutic benefit. The agent pimagidine (aminoguanidine), and other related compounds, have been found to be useful glycation inhibitors. This compound, and others like it, has been theorized to react with the carbonyl moiety of the early glycosylation product of a target protein formed subsequent to the initial non-enzymatic reaction with glucose or another reducing sugar, and thereby prevent further reaction to form advanced glycosylation end products.

The reaction of glucose with an amino group such as the ε-amine of a protein-bound lysine residue forms an aldimine, or Schiff base, which can then undergo Amadori rearrangement to Nε-(1-deoxy-1-fructosyl)lysine, the so-called Amadori product (AP) (1). Known as either protein glycation or protein glycosylation, this process occurs in vivo or in vitro. Hemoglobin $A_{1c}$ is an example of a glycated protein found in vivo; it is used as a marker of diabetic glucose control indicating the average glucose level over the preceding several weeks. Further poorly understood reactions of AP lead to the formation of advanced glycation endproducts products (AGEs) which can be colored or fluorescent and which can contain electrophilic centers which can cross-link two proteins together. Substantial evidence exists that such processes contribute to the pathology of diabetes and aging.

AGEs are usually formed only in tiny amounts relative to starting materials or early glycation products, from which they must be separated for structural characterization. Often, arbitrary distinguishing criteria such as fluorescence or color must be used to determine what components may be of interest. However, in recent years it has become apparent that protein cross-linking caused by advanced glycation is due primarily to unknown structures which are not highly colored or fluorescent.

Recently, it has been discovered that other naturally-occurring reducing sugars, including fructose, ribose and galactose, participate in non-enzymatic glycation and cross-linking. Thus, the formation of equivalent AGEs with fructose and other reactive sugars present in vivo or in foodstuffs, including ribose and galactose, are anticipated in the present invention.

SUMMARY OF THE INVENTION

In accordance with the present invention, model advanced glycosylation endproducts (AGEs) have been prepared which examine the AGE formation pathway wherein the Amadori Product (AP) is doubly dehydrated to form the AP-ene-dione and proceeds further to form advanced glycation endproducts. The thus prepared AGEs find utility as both therapeutic and diagnostic agents, and the present invention also concerns their methods of use in these areas.

The present invention also has particular diagnostic applications as the Maillard process acutely affects several of the significant protein masses in the body, among them collagen, elastin, lens proteins, and the kidney glomerular basement membranes. These proteins deteriorate both with age (hence the application of the term "protein aging") and as one of the sequelae of diabetes melitis. Consequently, the ability to measure the amount of the formation of advanced glycosylation end products carries the promise of favorably treating significant adverse effects of aging and of diabetes at an earlier stage, and, of course, improving the quality and perhaps duration of animal life, including for instance human life.

Accordingly, it is a principal object of the present invention to provide a method for measuring the extent of cross-linking of amino-containing peptides, proteins, biomolecules or other compounds that occurs as an ultimate consequence of the reaction of said peptides, proteins, biomolecules or other compounds with glucose or other reducing sugars, by measuring therein the corresponding formation of the advanced glycosylation end products of the present invention. This method finds particular use, among other applications, in the diagnosis of glycation-related disease and the monitoring of anti-glycation therapy or prophylactic treatment.

It is a further object of the present invention to provide therapeutic methods which comprise administration of the advanced glycosylation products of the present invention to mammals in order to activate the mammalian macrophage system to increase its activity of recognizing and removing such advanced glycosylation endproducts.

It is a still further object of the present invention to provide diagnostic methods for screening for and measuring the extent of the adverse consequences of aging, manifest, for instance, in the stiffening and embrittlement of animal protein and the browning and spoilage of foodstuffs and other comestibles by measuring the amount of advanced glycosylation endproducts.

Other objects and advantages will become apparent to those skilled in the art from a consideration of the ensuing description.

DETAILED DESCRIPTION OF THE INVENTION

In accordance with the present invention, a directed approach to identifying glycation-derived cross-linking species or immunoactive moieties was employed by an investigation of the AGE formation pathway shown in Scheme 1 below, in which dehydration of propyl-AP at the 4-position produces the AP-2,3-dione 2, and subsequent dehydration at the 5-position gives the AP-enedione 3.

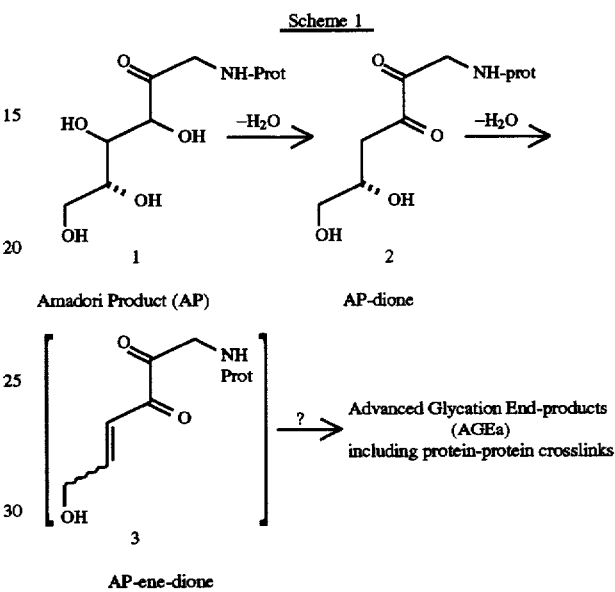

This AGE formation pathway has been little studied, and 3 has only been isolated in low yield as a tri-acetylated derivative. See, Estendorfer et al., *Angew. Chem. Int. Ed. Engl.* 1990, 29, 536. However, 3 should be a highly reactive electrophile; its γ-hydroxy α,β-unsaturated ketone moiety bears structural analogy to the lipid peroxidation product, 4-hydroxy-2-nonenal, which is known to be capable of Michael addition at the β-ene position by nucleophilic amino acid residues of proteins. Therefore, a synthetic precursor of 3, the Amadori product 4,5-ditosylate 4 was designed. Through successive β-eliminations of tosylate from 4 under neutral to basic conditions, 3 would be readily available in situ

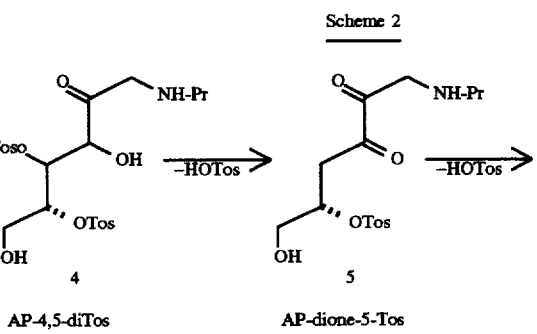

-continued
Scheme 2

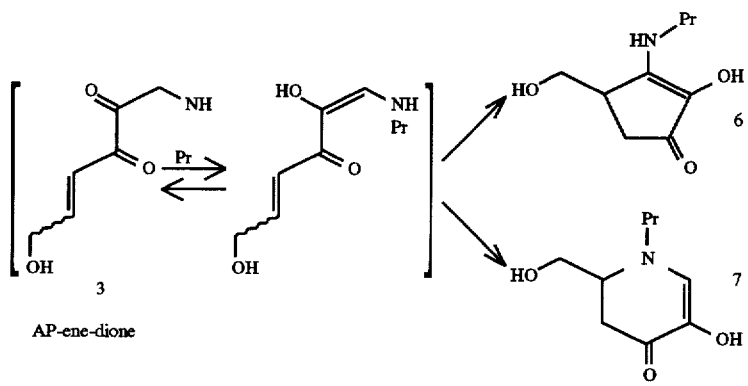

AP-ene-dione

In the absence of other nucleophiles, 3 could be expected to undergo internal β-addition reactions of C-1 or the 1-amine to the C-5 position to form two products: a 3-alkylamino-2-hydroxy-4-hydroxymethyl-2-cyclopenten-1-one 6 (the N-propyl derivative of a new type of aminoreductone, trivially named "cypentodine"), and the known 2-(hydroxymethyl)-4,5-piperidinedione enol 7 (see Scheme 2). Solvolysis of 4 leads to formation of these compounds.

The compound 4a, the pyranose form of 4, was synthesized from the propylamine Amadori product 1-deoxy-1-propylamino-β-D-fructopyranose hydrogen oxalate (8) or 2,3:4,5-di-O-isopropylidene-aldehydo-β-D-arabino-hexos-2-ulo-2,6-pyranose (9) in 77% or 81% overall yield, respectively. Reductive amination of protected aldehyde 9 with propylamine gave 10 in 95% yield. Compound 10 was also obtained by treating propylamine Amadori product 8 with concentrated $H_2SO_4$ in acetone in 90% yield. Selective removal of the 4,5-isopropylidene group to afford 11 was achieved by treating 10 with 1N HCl in a mixture of methanol and water (1:1) in 90% yield. Subsequent protection of the amine by reaction with di-t-butyl dicarbonate gave t-BOC derivative 12 in quantitative yield. Treatment of 12 with p-toluenesulfonylchloride in anhydrous pyridine gave the ditosylate 13 quantitatively. Removal of t-BOC and 2,3-isopropylidene groups in 1N HCl at 50° C. gave target compound 4a in 95% yield. The novel 6 as well as the known 7 were formed in 3:2 ratio (est. total yield 90% by HPLC) after incubation of 4a in phosphate buffer (0.5M, pH 7.4) and methanol (1:1) under nitrogen (Scheme 3). The major product (6) with-UV absorption maximum at 295 nm and the minor product (7) with UV absorption maximum at 360 nm were isolated by semi-preparative HPLC and the structures were assigned on the basis of spectral data.

The piperdinedione enol 7 has been reported to be formed in minor amount along with 2 in the degradation of a maltose-derived Amadori product at 100° C. in phosphate buffer.

It can be appreciated that although the propyl derivative is shown in the description and schemes herein, the other lower alkyl derivatives can similarly be produced by substitution of the appropriate starting material. Thus produced will be the 3-lower alkylamino-2-hydroxy-4-hydroxymethyl-2-cyclopenten-1-one derivatives wherein the lower alkyl group contains from 1 to 6 carbon atoms, and is exemplified by methyl, ethyl, propyl, butyl, pentyl and hexyl, and the corresponding branched chain isomers thereof.

Thus, the present invention is directed to compounds of the formula

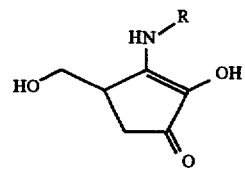

wherein R is a lower alkyl group containing from 1 to 6 carbon atoms.

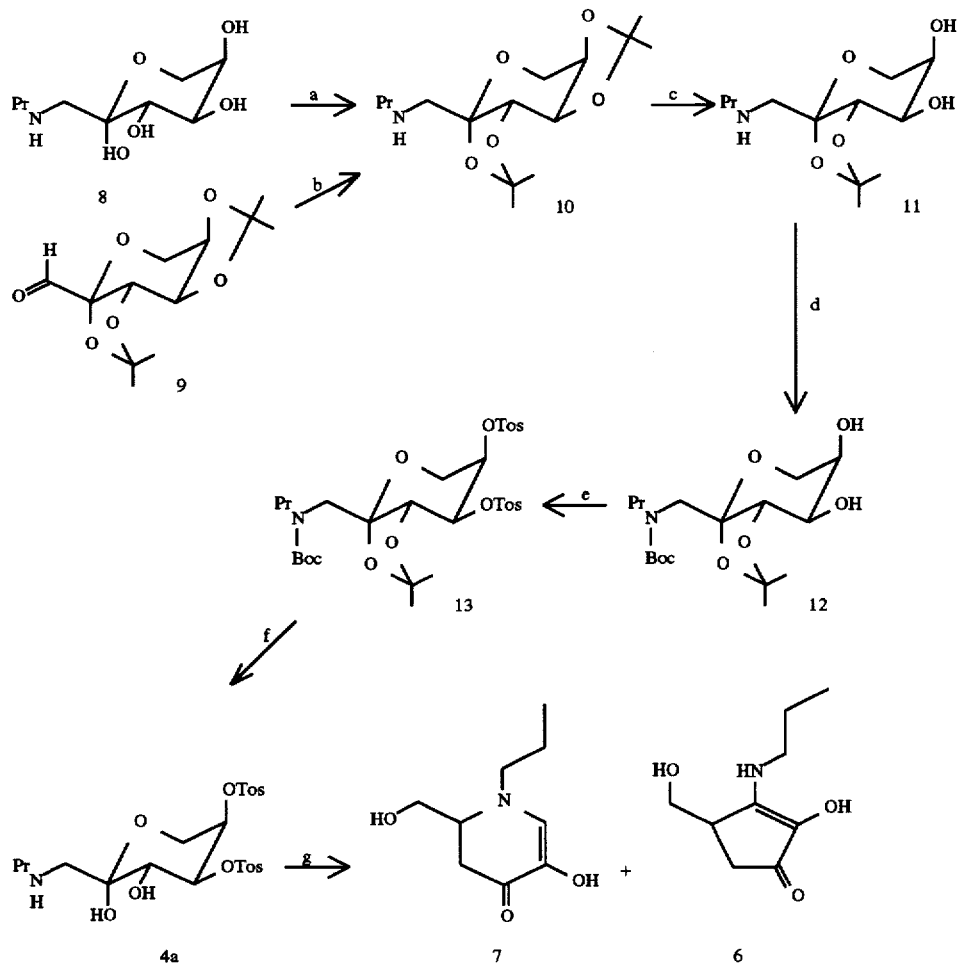

Scheme 4 shows how the enol of AP-ene-dione 3 can undergo internal cyclization in two ways: via attack of C-1 of the enol (path A) or the amine

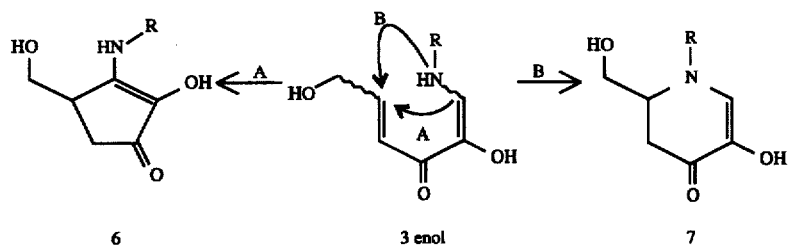

nitrogen (path B) at C-5 of the enone carbon-carbon double bond, to give 6 and 7, respectively. Although an alternative pathway involving internal $S_N2$ displacement of tosylate in intermediate 5 cannot be ruled out at this time, it seems likely that β-elimination of the tosylate of 5 would be a more rapid process. Moreover, the reported isolation of 7 along with 2 (as its enol triacetyl derivative) from the degradation products of an Amadori product of maltose on heating at neutral pH lends support to the intermediacy of AP-ene-dione 3 in the formation of cyclization products 6 and 7 from the ditosylate 4.

To further elucidate the mechanism of these reactions, the 4-O-mono-tosylate of Amadori product 8 can be synthesized. The cross-linking potential of AP-ene-dione 3 can be clarified by studies of model cross-linking reactions of 3 (via solvolysis of 4), 6, and 7 with various nucleophiles. The presence of cypentodine (6) among the various solvolysis products which slowly form during incubation of propyl Amadori product 8 by itself under physiological conditions, and in the complex mixtures which form in the classical Maillard reaction conditions of incubation of glucose with amines can be utilized is the basis for the diagnostic methods of the present invention.

In the instance where the present invention has therapeutic applications, the animal host intended for treatment may have administered to it a quantity of the advanced glycosylation endproduct of formula 6, either as a free cyclic pentosidine compound or formed within the sequence of a longer peptide or peptide-like molecule, in a suitable pharmaceutical form. Such administration can increase the macrophage recognition and elimination of other advanced glycosylation endproducts in the mammalian body. Administration may be accomplished by known techniques, such as oral, topical and parenteral techniques such as intradermal, subcutaneous, intravenous, or intraperitoneal injection, as well as by other conventional means such as inhaled aerosols or nebulized droplets. Administration of the agents may take place over an extended period of time at a dosage level of, for example, up to about 25 mg/kg.

The ability to measure the formation of advanced glycosylation end products carries with it significant implications in all applications where protein aging is a serious detriment. Thus, in the area of food technology, the facile determination of the amount of food spoilage allows for social benefit by ensuring that potentially harmful food products can be removed from use in a timely fashion. The expense of inspection, removal and replacement of the foods would be reduced due to the ease of making such determinations. Similarly, in other industrial applications where the perishability of proteins or other amino-containing biomolecules (e.g. lipids and DNA) or compounds (e.g. pharmaceutical compositions) is a problem, a measurement of the amount of AGE formation will provide a low-cost and facile method of determining shelf-life.

Accordingly, the compositions useful in the present invention comprise the compound of formula 6, together with carriers suitable for their intended use.

The findings of the present invention can also be utilized to screen for additional agents which would have utility as agents for inhibiting advanced glycosylation or glycation. Thus, the measurement of the amount of the formation of the compound of formula 6 when exposed to an amount of a potential inhibitor of the advanced glycosylation reaction, would enable one to assess the usefulness of an agent as a potential inhibitor of the advanced glycosylation or glycation process.

The compounds of formula 6 may be used in standard fashion to prepare either polyclonal or monoclonal antibodies thereto for diagnostic purposes. Such antibodies are preparable by standard procedures, and thus enable the use of diagnostic assays for assessing and monitoring the effectiveness of therapeutic regimens where AGE inhibition has been initiated. Said immunological regents directed against generic and specific structures of the present invention are also useful to detect the degree of advanced glycosylation in a sample from a subject animal, including, for example, a human being, thereby to infer degree of advanced glycosylation which has occurred in the subject, by reference to a standard. Said polyclonal or monoclonal immunological reagents can optionally be included in a kit, with instructions, and, optionally, a standardized preparation of a cyclic pentosidine compound of the present invention, to facilitate such determinations all as contemplated hereunder.

In the instance where the composition of the present invention is utilized for in vivo or therapeutic purposes, it may be noted that the compounds or agents used therein are biocompatible. Pharmaceutical compositions may be prepared with a pharmaceutically effective quantity of the agents or compounds of the present invention and may include a pharmaceutically acceptable carrier, selected from known materials utilized for this purpose. Such compositions may be prepared in a variety of forms, depending on the method of administration. For example, a liquid form would be utilized in the instance where administration is by intravenous or intraperitoneal injection, which liquid might be aerosolized for delivery by inhalation; while, if appropriate, tablets, capsules, etc., may be prepared for oral administration. For application to the skin, a lotion or ointment may be formulated with the agent in a suitable vehicle, perhaps including a carrier to aid in penetration into the skin. Other suitable forms for administration to other body tissues are also contemplated.

In the instance where therapeutic applications are intended, the animals to be treated would have administered to them a regular quantity of the pharmaceutical composition of the present invention. Administration could take place, for example, daily, and an effective quantity of the agent or compound of the present invention could range up to 25 mg/kg of body weight of the animal. A topical preparation may, for example, include up to 10% of the agent or composition in an ointment or lotion for application to the skin. Naturally, some variation in these amounts is possible, and the suggested amounts are provided in fulfillment of applicants' duty to disclose the best mode for the practice of the present invention.

The in vivo therapeutic implications of the present invention relate to the reversal of several of the pathogenic activities associated with the aging process which have, as indicated earlier, been identified in the aging of key tissue and circulating proteins by advanced glycosylation and crosslinking through the mechanism of macrophage stimulation of the removal of the advanced glycosylation endproducts. Thus, body proteins, and particularly structural body proteins such as collagen, elastin, lens proteins, nerve proteins and kidney glomerular basement membranes would all benefit in their longevity and operation from the practice of the present invention. The present invention thus reduces the senescence caused by pathologies involving the entrapment of proteins by crosslinked target proteins, as exemplified, for instance, in retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence in patients afflicted with diabetes mellitus. Thus, the present therapeutic method is relevant to treatment of the noted conditions in patients either of advanced age or those suffering from one of the mentioned pathologies, particularly in association with hyperglycemia, which accelerates glycation-mediated senescence.

Protein crosslinking through advanced glycosylation product formation can decrease solubility of structural proteins such as collagen in vessel walls, and as well as trap serum proteins, such as lipoproteins to structural proteins such as collagen. Also, this may result in covalent trapping of extravasated plasma proteins in subendothelial matrix, and reduction in susceptibility of both plasma and matrix proteins to physiological degradation by enzymes. For these reasons, the progressive occlusion of diabetic vessels induced by chronic hyperglycemia has been hypothesized to result in part from excessive formation of glucose-derived adducts and crosslinks. Such diabetic macrovascular changes and microvascular occlusion can be effectively treated by enhancing the removal of advanced glycosylation endproducts utilizing a composition and the methods of the present invention.

The present invention will be better understood from a consideration of the following illustrative examples, reviewing the selection and testing of certain of the agents of the present invention on both an in vitro and in vivo basis.

This invention may be embodied in other forms or carried out in other ways without departing from the spirit or essential characteristics thereof. The present disclosure is therefor to be considered as in all respects illustrative and not restrictive, the scope of the invention being indicated by the appended Claims, and all changes which come within the meaning and range of equivalency are intended to be embraced therein.

EXAMPLE 1

The compound 4a, the pyranose form of 4, was synthesized from the propylamine Amadori product 1-deoxy-1-propylamino-β-D-fructopyranose hydrogen oxalate (8) or 2,3:4,5-di-O-isopropylidene-aldehydo-β-D-arabino-hexos-2-ulo-2,6-pyranose (9) in 77% or 81% overall yield, respectively. 4a $^1$HNMR δ0.87 (t, 3H, $CH_3CH_2$), 1.33 (s, 3H, $CH_3CMe$), 1.40 (s, 3H, $CH_3CMe$), 1.42 (s, 9H, t-Bu), ca. 1.3–1.5 (m, 2H, $CH_3CH_2$), 2.46 (s, 6H,$CH_3C_6H_4$), ca. 3.15 (m, 2H, H(1a)+$CH_2CH^aH^bN$), ca. 3.35 (m, 1H, $CH_2CH^aH^bN$), 3.60 (dd, 1H, H (6a)), 3.9–4.3(complex m, 3H, H(1b)+H(3)+H(6b)), 4.69 (m, 1H, H (5)), 4.87 (br m, 1H, H (4)), ca. 7.3 (2d, 4H, meta to $SO_2$), 7.60 (d, 2H, ortho to $SO_2$), 7.81 (d, 2H, ortho to $SO_2$).

Reductive amination of protected aldehyde 9 with propylamine gave 10 in 95% yield. Compound 10 was also obtained by treating propylamine Amadori product 8 with concentrated $H_2SO_4$ in acetone in 90% yield. Selective removal of the 4,5-isopropylidene group to afford 11 was achieved by treating 10 with 1N HCl in a mixture of methanol and water (1:1) in 90% yield. Subsequent protection of the amine by reaction with di-t-butyl dicarbonate gave t-BOC derivative 12 in quantitative yield. Treatment of 12 with p-toluenesulfonylchloride in anhydrous pyridine gave the ditosylate 13 quantitatively. Removal of t-BOC and 2,3-isopropylidene groups in 1N HCl at 50° C. gave target compound 4a in 95% yield. The novel 6 as well as the known 7 were formed in 3:2 ratio (est. total yield 90% by HPLC) after incubation of 4a in phosphate buffer (0.5M, pH 7.4) and methanol (1:1) under nitrogen (Scheme 3). The major product (6) with UV absorption maximum at 295 nm and the minor product (7) with UV absorption maximum at 360 nm were isolated by semi-preparative HPLC and the structures were assigned on the basis of spectral data. 6 $^1$HNMR ($CD_3OD$) :0.95 (t, 3H, $CH_2CH_3$), 1.60 ) (q, 2H, $NHCH_2CH_2CH_3$), 2.08 (dd, 17.5 Hz, 1.7 Hz, 1H $CHaH_bCO$), 2.80 (m, 1H, $COCH_2CH$), 3.5 (t, $NHCH_2CH_2$), 3.59 (dd, 10.8 Hz, 5.9 Hz, 1H, $CH_aH_bOH$), 3.69 (dd, 10.8 Hz, 5.4 Hz, 1H, $CHaH_bOH$). $^{13}$C-NMR ($CD_3OD$) : 10.5 ($CH_2CH_3$), 24.3 ($CH_2CH_3$), 33.6 ($COCH_2$), 37.8 ($CH_2CH$), 45.2 (NHC), 63.8 ($CH_2OH$), 128.5 ($N_2C=COH$), 160.4 ($NH_2C=COH$), 193.2 (C=O) MS (FAB+) m/z: 186 ($MH_+$), 100%). HRMS ($FAB_+$) m/z: 186.1128 (calcd for $C_9H_{15}NO_3=H_+$, 186.1130).

UV, $^1$H NMR, and $^{13}$C NMR spectroscopic properties were in accord with literature precedent for the N-butyl analog of compound 7 (Ref. 11). The piperdinedione enol 7 has been reported to be formed in minor amount along with 2 in the degradation of a maltose-derived Amadori product at 100° C. in phosphate buffer.

EXAMPLE 2

Antigens, and conjugated immunogens corresponding to the cyclic pentosidine-like advanced glycosylation endproducts of the present invention, including the products described in Example 1 can conveniently be prepared, either by isolation from incubation mixtures or by direct synthetic approaches. The AGEs thus prepared may then be used as an immunogens to raise a variety of antibodies which recognize specific epitopes or molecular features thereof. In a preferred embodiment, the 3-alkylamino-2-hydroxy-4-hydroxymethyl-2-cyclopenten-1-one itself is considered a hapten, which is correspondingly coupled to any of several preferred carrier proteins, including for instance keyhole limpet hemocyanin (KLH), thyroglobulin, and most preferred, bovine serum albumin (BSA), using any of a number of well-known rivalent coupling reagents such as a carbodiimide like EDC, according to protocols widely circulated in the art. Irrespective of the source, the 3-alkylamino-2-hydroxy-4-hydroxymethyl-2-cyclopenten-1-one-like AGE of formula 6, alone or coupled to a carrier protein, may be employed in any well-recognized immunization protocol to generate antibodies and related immunological reagents that are useful in a number of applications owing to the specificity of the resulting antibodies for molecular features of the 3-alkylamino-2-hydroxy-4-hydroxymethyl-2-cyclopen-1-one-like AGE of formula 6.

Following a preferred protocol, any of several animal species may be immunized to produce polyclonal antisera directed against the cypentodine-carrier protein conjugate, including for instance mice, rats, hamsters, goats, rabbits, and chickens. The first of three of the aforesaid animal species are particularly desirable choices for the subsequent production of hybridomas secreting hapten-specific monoclonal antibodies. The production of said hybridomas from spleen cells of immunized animals may conveniently be accomplished by any of several protocols popularly practiced in the art, and which describe conditions suitable for immortalization of immunized spleen cells by fusion with an appropriate cell line, e.g. a myeloma cell line. Said protocols for producing hybridomas also provide methods for selecting and cloning immune splenocyte/myeloma cell hybridomas and for identifying hybridomas clones that stably secrete antibodies directed against the desired epitope(s). Animal species such as rabbit and goat are more commonly employed for the generation of polyclonal antisera, but regardless of whether polyclonal antisera or monoclonal antibodies are desired ultimately, the hapten-modified carrier protein typically is initially administered in conjunction with an adjuvant such as Complete Freund's Adjuvant. Immunizations may be administered by any of several routes, typically intraperitoneal, intramuscular or intradermal; certain routes are preferred in the art according to the species to be immunized and the type of antibody ultimately to be produced. Subsequently, booster immunizations are generally administered in conjunction with an adjuvant such as alum or Incomplete Freund's Adjuvant. Booster immunizations are administered at intervals after the initial immunization; generally one month is a suitable interval, with blood samples taken between one and two weeks after each booster immunization. Alternatively, a variety of so-called hyperimmunization schedules, which generally feature booster immunizations spaced closer together in time, are sometimes employed in an effort to produce anti-hapten antibodies preferentially over anti-carrier protein antibodies.

The antibody titers in post-boost blood samples can be compared for hapten-specific immune titer in any of several convenient formats including, for instance, Ouchterlony diffusion gels and direct ELISA protocols. In a typical direct ELISA, a defined antigen is immobilized onto the assay well surface, typically in a 96-well microtiter plate format, followed by a series of incubations separated by rinses of the assay well surface to remove unbound binding partners. By way of non-limiting example, the wells of an assay plate may receive a dilute, buffered aqueous solution of the hapten/carrier conjugate, preferably wherein the carrier protein differs from that used to immunize the antibody-producing animal to be tested; e.g. serum from cypentodine/KLH conjugate-immunized animal might be tested against assay wells decorated with immobilized cypentodine/BSA conjugate. Alternatively, the assay surface may be decorated by incubation with the hapten alone. Generally, the surface of the assay wells is then exposed to a solution of an irrelevant protein, such as casein, to block unoccupied sites on the plastic surfaces. After rinsing with a neutral buffered solution that typically contains salts and a detergent to minimize non-specific interactions, the well is then contacted with one of a serial dilution of the serum prepared from the blood sample of interest (the primary antiserum in crude or purified form). After rinsing again, the extent of test antibodies immobilized onto the assay wells by interaction with the desired hapten or hapten/carrier conjugate can be estimated by any of a number of well known procedures including, for instance incubation with a commercially available enzyme-antibody conjugate, wherein the antibody portion of this secondary conjugate is directed against the species used to produce the primary antiserum; e.g. if the primary antiserum were raised in rabbits, a commercial preparation of anti-rabbit antibodies raised in goat and conjugated to one of several enzymes, such as horseradish peroxidase, can be used as the secondary antibody. Following procedures specified by the manufacturer, the amount of this secondary antibody can then be estimated quantitatively by the activity of the associated conjugate enzyme in an assay, typically a colorimetric assay. Many related ELISA or radioimmunometric protocols, such as competitive ELISAs or sandwich ELISAs, all of which are well-known in the art, may optionally be substituted, to identify the desired antisera of high liter; that is, the particular antiserum which gives a true positive result at high dilution (e.g. greater than 1/1000 and more preferably to greater than 1/10,000).

Similar immunometric protocols can be used to estimate the titer of antibodies in culture supernatants from hybridomas prepared from spleen cells of immunized animals. In so characterizing antisera or hybridoma supernatants, it is desirable to employ a variety of control incubations, e.g. with different carrier proteins, related but structurally distinct haptens or antigens, and omitting various reagents in the immunometric procedure in order to minimize non-specific signals in the assay and to identify reliable determinations of antibody specificity and liter from false positive and false negative results. The types of control incubations to use in this regard are well known. Also, the same general immunometric protocols subsequently may be employed with the antisera identified by the above procedures to be of high titer and to be directed against specific structural determinants of cypentodine-like AGEs present in biological samples, foodstuffs or other comestibles, or other amine-bearing substances and biomolecules of interest. Such latter applications of the desired antibodies, whether polyclonal or monoclonal, together with instructions and optionally with other useful reagents and diluents, including, without limitation, a set of molecular standards of cypentodine-like AGEs, may be provided in kit form for the convenience of the operator.

What is claimed is:

1. A compound of the formula 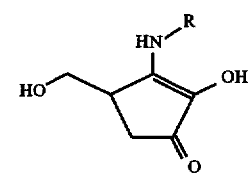 wherein R is a lower alkyl group containing from 1 to 6 carbon atoms.

2. An antibody to the compound of claim 1.

3. A kit for the detection of the compounds of claim 1, comprising the antibody of claim 2.

* * * * *